United States Patent
Hancock

(10) Patent No.: US 12,064,173 B2
(45) Date of Patent: Aug. 20, 2024

(54) ELECTROSURGICAL APPARATUS

(71) Applicant: Creo Medical Limited, Chepstow Monmouthshire (GB)

(72) Inventor: Christopher Paul Hancock, Bath (GB)

(73) Assignee: CREO MEDICAL LIMITED, Chepstow (GB)

( * ) Notice: Subject to any disclaimer, the term of this patent is extended or adjusted under 35 U.S.C. 154(b) by 681 days.

(21) Appl. No.: 16/758,359

(22) PCT Filed: Dec. 20, 2018

(86) PCT No.: PCT/EP2018/086234
§ 371 (c)(1),
(2) Date: Apr. 22, 2020

(87) PCT Pub. No.: WO2019/129647
PCT Pub. Date: Jul. 4, 2019

(65) Prior Publication Data
US 2020/0337767 A1    Oct. 29, 2020

(30) Foreign Application Priority Data

Dec. 27, 2017  (GB) ..................................... 1721994

(51) Int. Cl.
*A61B 18/18*     (2006.01)
*H03F 3/19*      (2006.01)
*A61B 17/00*     (2006.01)

(52) U.S. Cl.
CPC ............ *A61B 18/1815* (2013.01); *H03F 3/19* (2013.01); *A61B 2017/00181* (2013.01); *A61B 2018/1823* (2013.01)

(58) Field of Classification Search
CPC ........ A61B 18/1515; A61B 2018/1823; A61B 2017/00181; H03F 3/19
See application file for complete search history.

(56) References Cited

U.S. PATENT DOCUMENTS

2003/0215373 A1    11/2003  Reyzelman et al.
2004/0138654 A1*    7/2004  Goble ................ A61B 18/1206
                                                        606/41
(Continued)

FOREIGN PATENT DOCUMENTS

CN         101908895 A    12/2010
EP         3170256 A1      5/2017

OTHER PUBLICATIONS

Kanto K et al. (2008). "An X-band 250W solid-state power amplifier using GaN power HEMTs." In 2008 IEEE Radio and Wireless Symposium. 2008 IEEE Radio and Wireless Symposium. IEEE. https://doi.org/10.1109/rws.2008.4463432 (Year: 2008).*

(Continued)

*Primary Examiner* — Sean W Collins
*Assistant Examiner* — Rachel A. Vierra
(74) *Attorney, Agent, or Firm* — ArentFox Schiff LLP

(57) ABSTRACT

An apparatus capable of generating high power microwave frequency pulses for use with an electrosurgical device. The apparatus may be used for coagulating or ablating biological tissue. The apparatus includes an amplifier line-up comprising: a microwave signal generator for generating microwave radiation; a modulator arranged to pulse the microwave radiation; and an amplifier module arranged to increase the power of pulses of microwave radiation. The amplifier module works by providing a set of amplifiers that exhibit a gain that is greater than the total loss experienced at the components that divide the input signal and then combine the output signals. For example, if each amplifier in the array has a gain of 10 dBm, it is viable to use conventional power splitters and combiners to obtain an output microwave signal with substantially higher power than is provided by conventional electrosurgical generators.

11 Claims, 3 Drawing Sheets

(56) References Cited

U.S. PATENT DOCUMENTS

| | | |
|---|---|---|
| 2005/0149012 A1 | 7/2005 | Penny et al. |
| 2006/0155270 A1 | 7/2006 | Hancock et al. |
| 2010/0036369 A1* | 2/2010 | Hancock ............ A61B 18/1815 606/33 |
| 2010/0168727 A1* | 7/2010 | Hancock ................ A61B 18/18 606/33 |
| 2013/0267943 A1* | 10/2013 | Hancock ............ A61B 18/1206 606/33 |
| 2014/0028398 A1 | 1/2014 | Owen |
| 2016/0155270 A1 | 6/2016 | Poulos et al. |
| 2016/0359460 A1 | 12/2016 | Garuti et al. |
| 2016/0374752 A1 | 12/2016 | Hancock et al. |
| 2018/0243558 A1* | 8/2018 | Athos ................ A61B 18/1206 |

OTHER PUBLICATIONS

International Preliminary Report on Patentability issued from the International Preliminary Examining Authority in corresponding International Application No. PCT/EP2018/086234, mailed on Feb. 25, 2020.

International Search Report and Written Opinion issued by the International Searching Authority in corresponding International Patent No. PCT/EP2018/086234, mailed Apr. 4, 2019.

Kanto, K., et al., "An X-band 250W Solid-State Power Amplifier using GaN Power HEMTs", Radio and Wireless Symposium, XP031237102, pp. 77-80, (Jan. 22, 2008).

Search Report issued by the United Kingdom Intellectual Property Office in corresponding United Kingdom Patent Application No. 1721994.0, dated May 29, 2018.

* cited by examiner

ELECTROSURGICAL APPARATUS

CROSS-REFERENCE TO RELATED APPLICATIONS

This application is a National Stage entry of International Application No. PCT/EP2018/086234, filed on Dec. 20, 2018, which claims priority to British Patent Application No. 1721994.0, filed on Dec. 27, 2017. The disclosures of the priority applications are hereby incorporated in their entirety by reference.

FIELD OF THE INVENTION

The invention relates to an electrosurgical apparatus in which microwave frequency energy is used to treat biological tissue. In particular, the invention relates to an amplifier line-up for an electrosurgical generator capable of generating high power microwave frequency pulses for coagulation or ablation of biological tissue.

BACKGROUND TO THE INVENTION

It is known to use microwave emitting probes to treat various conditions in the lungs and other body tissues. For example, in the lungs, microwave radiation can be used to treat asthma and ablate tumours or lesions.

GB 2 486 343 discloses a control system for an electrosurgical apparatus which delivers both RF and microwave energy to treat biological tissue. The energy delivery profile of both RF energy and microwave energy delivered to a probe is set based on sampled voltage and current information of RF energy conveyed to the probe and sampled forward and reflected power information for the microwave energy conveyed to and from the probe.

SUMMARY OF THE INVENTION

At its most general, the present invention provides an apparatus capable of generating high power microwave frequency pulses for use with an electrosurgical device. The apparatus may be used for treating, for example coagulating or ablating, biological tissue.

According to the invention, there is provided an amplifier line-up for an electrosurgical generator, the amplifier line-up comprising: a microwave signal generator for generating microwave electromagnetic (EM) radiation; a modulator arranged to pulse the microwave EM radiation; and an amplifier module connect to the modulator and arranged to increase the power of pulses of microwave EM radiation received therefrom, the amplifier module comprising an array of amplifiers connected in parallel, wherein output signals from the array of amplifiers are combined to produce an output microwave signal; and a feed structure for conveying the output microwave signal to a probe. The amplifier module works by providing a set of amplifiers that exhibit a gain that is greater than the total loss experienced at the components that divide the input signal and then combine the output signals. For example, if each amplifier in the array has a gain of 10 dBm, it is viable to use conventional power splitters and combiners to obtain a output microwave signal with substantially higher power than is provided by conventional electrosurgical generators.

The invention proposes an amplifier line-up that delivers a given energy payload as a series of short-duration high-power pulses. The target tissue receives the energy payload and therefore exhibits a desired ablation effect. For example a 2 kJ energy payload may create a lesion of around 3.5 cm in diameter in biological tissue. However, the duration and magnitude of the pulses may be selected both to ensure a relatively short overall treatment time, whilst also minimising effects (e.g. thermal losses) associated with the feed structure.

It is desirable to have a shorter overall treatment time both for patient comfort and to avoid unwanted thermal effects associated with perfusion in tissue. Given a target energy payload of 2 kJ, one can consider delivered this as 20 W continuous wave signal for 100 s, or as a series of short 2 kW pulses spread over a much shorter period, e.g. equal to or less than 10 s. Continuous delivery of energy for 100 second may lead to patient discomfort and the transfer of energy away from the target site by perfusion. These effects are reduced by the use of the pulsed technique proposed herein. Moreover, since the human body exhibits a non-zero reaction time in detecting and responding to received energy, especially thermal energy, applying high levels of energy in short bursts (e.g. having a duration equal to or less the body's reaction time), the body may not have enough time to execute its natural thermal compensation mechanisms. Since these mechanisms (e.g. increased blood flow to skin surface, etc.) act to transfer thermal energy away from a heated region, the act of bypassing them enables the invention to provide more accurately targeting or localization of delivered energy.

Similar effects apply to the structure for conveying the energy. For example, a cable carrying a 20 W continuous wave signal will heat up significantly over a 100 s treatment period. By utilising the pulsed technique proposed herein, those thermal effects can be reduced by delivering the energy in pulses having a duration that is quicker than the thermal response of the cable. Put simply, by shortening the time at which power is actually transmitted by the cable and by shortening the overall treatment time, unwanted thermal effects can be reduced or avoided.

A further advantage of reducing the treatment time, is that it allows smaller diameter coaxial cables (which typically exhibit higher loss) to be used. This allows insertion of the probe into smaller biological structures or cavities.

The amplifier module may comprise a power divider unit arranged to receive the pulses of microwave EM radiation from the modulator and split then into input signals for the array of amplifiers. Similarly the amplifier module may comprise a power combiner unit arranged to combine the output signals from the array of amplifiers. The power divider unit and power combiner unit may be symmetrically arranged. The power divider unit may have a single one-to-many stage, or a plurality of cascading stages.

The line up may comprise a drive amplifier connected between the modulator and the amplifier module, e.g. to ensure that the microwave EM radiation supplied to the amplifier module has an appropriate power.

The input pulses remain synchronised through the amplifier module so that the amplified output signal combine additively. The output microwave signal (i.e. the combined signal) may comprise a series of microwave pulses each having a power equal to or greater than 400 W, and preferably equal to or greater than 2 kW. The microwave pulses may each have a duration equal to or less than 0.1 s, preferably equal to or less than 1 ms. The output microwave signal may have a duty cycle equal to or less than 50%, preferably equal to or less than 20%.

The magnitude (power), duration and duty cycle of the output microwave signal may be selectable, e.g. based on a target energy payload, to ensure that a total treatment time is less than a threshold. The threshold may be equal to or less than 20 seconds. In this way, high power microwave EM pulses may be delivered to tissue without significant heating of components making up the electrosurgical apparatus. This reduces the need for cooling systems, and may also help prolong the effective operating time and life span of the apparatus.

The array of amplifiers may comprise eight amplifiers. Preferably the amplifiers may comprise high electron mobility transistors (HEMTs). By using such transistors, the apparatus may operate efficiently and effectively at microwave frequencies with minimal losses, and the transistors may provide a large gain such that the amplifier circuit may require fewer amplifiers. For example, the transistors may be gallium nitride HEMTs. Each transistor may have a gain of at least 10 dBm, and may have an output power of at least 56 dBm or 400 W.

The feed structure may comprise a coaxial cable having a diameter equal to or less than 3 mm, preferably equal to or less than 2.2 mm.

In certain embodiments, the amplifier line-up may be used in an electrosurgical generator that also comprises a radiofrequency (RF) signal generator for generating RF EM radiation. The apparatus may, in such embodiments, comprise a RF feed structure for conveying the RF EM radiation to the probe, which may also be configured to deliver RF EM radiation.

The amplifier line-up may form part of an electrosurgical system that includes a probe connectable at a distal end of the feed structure. The probe may be insertable through an instrument channel of a surgical scoping device, such as an endoscope or bronchoscope. In this way, the apparatus may be used for endoscopic procedures. The term "surgical scoping device" may be used herein to mean any surgical device provided with an insertion tube that is a rigid or flexible (e.g. steerable) conduit that is introduced into a patient's body during an invasive procedure. The insertion tube may include the instrument channel and an optical channel (e.g. for transmitting light to illuminate and/or capture images of a treatment site at the distal end of the insertion tube. The instrument channel may have a diameter suitable for receiving invasive surgical tools. The diameter of the instrument channel may be 5 mm or less.

In this specification "microwave" may be used broadly to indicate a frequency range of 400 MHz to 100 GHz, but preferably the range 1 GHz to 60 GHz. Specific frequencies that have been considered are: 915 MHz, 2.45 GHz, 3.3 GHz, 5.8 GHz, 10 GHz, 14.5 GHz and 24 GHz. The device may delivery energy at more than one of these microwave frequencies. In contrast, this specification uses "radiofrequency" or "RF" to indicate a frequency range that is at least three orders of magnitude lower, e.g. up to 300 MHz, preferably 10 kHz to 1 MHz.

BRIEF DESCRIPTION OF THE DRAWINGS

Embodiments of the invention are described in detail below with reference to the accompanying drawings, in which.

DETAILED DESCRIPTION; FURTHER OPTIONS AND PREFERENCES

Background

Figure 1:
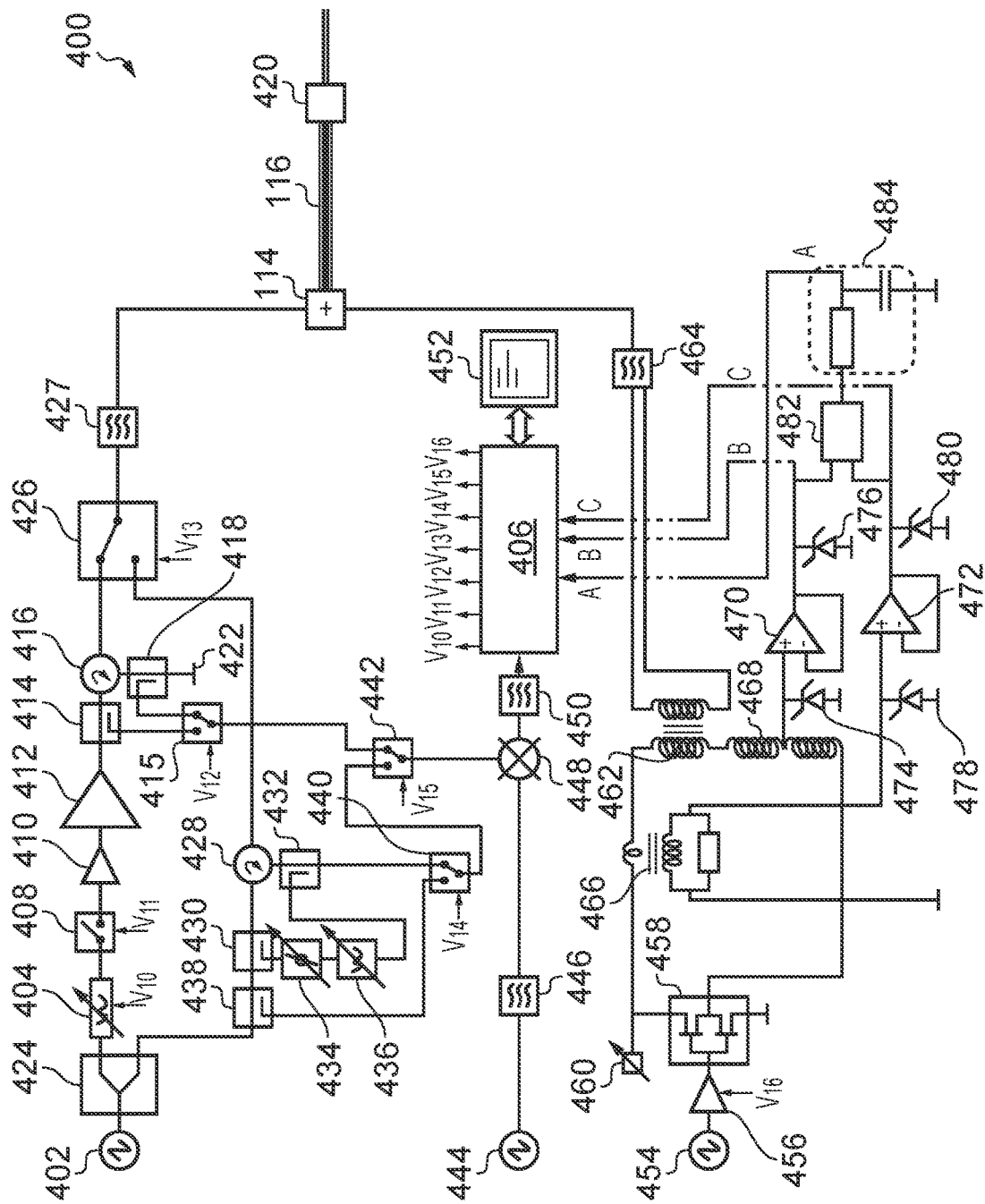
FIG. 1 is an overall schematic system diagram of a known electrosurgical apparatus.

FIG. 1 shows a schematic diagram of an electrosurgical apparatus 400, such as that disclosed in GB 2 486 343, that is useful for understanding the invention. The apparatus comprises a RF channel and a microwave channel. The RF channel contains components for generating and controlling an RF frequency electromagnetic signal at a power level suitable for treating (e.g. cutting or desiccating) biological tissue. The microwave channel contains components for generating and controlling a microwave frequency electromagnetic signal at a power level suitable for treating (e.g. coagulating or ablating) biological tissue.

The microwave channel has a microwave frequency source 402 followed by a power splitter 424 (e.g. a 3 dB power splitter), which divides the signal from the source 402 into two branches. One branch from the power splitter 424 forms a microwave channel, which has a power control module comprising a variable attenuator 404 controlled by controller 406 via control signal $V_{10}$ and a signal modulator 408 controlled by controller 406 via control signal $V_{11}$, and an amplifier module comprising drive amplifier 410 and power amplifier 412 for generating forward microwave frequency EM radiation for delivery from a probe 420 at a power level suitable for treatment. After the amplifier module, the microwave channel continues with a microwave signal coupling module (which forms part of a microwave signal detector) comprising a circulator 416 connected to deliver microwave frequency EM energy from the source to the probe along a path between its first and second ports, a forward coupler 414 at the first port of the circulator 416, and a reflected coupler 418 at the third port of the circulator 416. After passing through the reflected coupler, the microwave frequency EM energy from the third port is absorbed in a power dump load 422. The microwave signal coupling module also includes a switch 415 operated by the controller 406 via control signal $V_{12}$ for connecting either the forward coupled signal or the reflected coupled signal to a heterodyne receiver for detection.

The other branch from the power splitter 424 forms a measurement channel. The measurement channel bypasses the amplifying line-up on the microwave channel, and hence is arranged to deliver a low power signal from the probe. A primary channel selection switch 426 controlled by the controller 406 via control signal $V_{13}$ is operable to select a signal from either the microwave channel or the measurement channel to deliver to the probe. A high band pass filter 427 is connected between the primary channel selection switch 426 and the probe 420 to protect the microwave signal generator from low frequency RF signals.

The measurement channel includes components arranged to detect the phase and magnitude of power reflected from the probe, which may yield information about the material e.g. biological tissue present at the distal end of the probe. The measurement channel comprises a circulator 428 connected to deliver microwave frequency EM energy from the source 402 to the probe along a path between its first and second ports. A reflected signal returned from the probe is directed into the third port of the circulator 428. The circulator 428 is used to provide isolation between the forward signal and the reflected signal to facilitate accurate measurement. However, as the circulator does not provide complete isolation between its first and third ports, i.e. some of the forward signal may break through to the third port and interfere with the reflected signal, a carrier cancellation circuit may be used that injects a portion of the forward signal (from forward coupler 430) back into the signal coming out of the third port (via injection coupler 432). The carrier cancellation circuit include a phase adjustor 434 to ensure that the injected portion is 180° out of phase with any signal that breaks through into the third port from the first port in order to cancel it out. The carrier cancellation circuit also include a signal attenuator 436 to ensure that the magnitude of the injected portion is the same as any breakthrough signal.

To compensate for any drift in the forward signal, a forward coupler 438 is provided on the measurement channel. The coupled output of the forward coupler 438 and the reflected signal from the third port of the circulator 428 are connected to respective input terminal of a switch 440, which is operated by the controller 406 via control signal $V_{14}$ to connect either the coupled forward signal or the reflected signal to a heterodyne receiver for detection.

The output of the switch 440 (i.e. the output from the measurement channel) and the output of the switch 415 (i.e. the output from the microwave channel) are connected to a respective input terminal of a secondary channel selection switch 442, which is operable by the controller 406 via control signal $V_{15}$ in conjunction with the primary channel selection switch to ensure that the output of the measurement channel is connected to the heterodyne receiver when the measurement channel is supplying energy to the probe and that the output of the microwave channel is connected to the heterodyne receiver when the microwave channel is supplying energy to the probe.

The heterodyne receiver is used to extract the phase and magnitude information from the signal output by the secondary channel selection switch 442. A single heterodyne receiver is shown in this system, but a double heterodyne receiver (containing two local oscillators and mixers) to mix the source frequency down twice before the signal enters the controller may be used if necessary. The heterodyne receiver comprises a local oscillator 444 and a mixer 448 for mixing down the signal output by the secondary channel selection switch 442. The frequency of the local oscillator signal is selected so that the output from the mixer 448 is at an intermediate frequency suitable to be received in the controller 406. Band pass filters 446, 450 are provided to protect the local oscillator 444 and the controller 406 from the high frequency microwave signals.

The controller 406 receives the output of the heterodyne receiver and determines (e.g. extracts) from it information indicative of phase and magnitude of the forward and/or reflected signals on the microwave or measurement channel. This information can be used to control the delivery of high power microwave frequency EM radiation on the microwave channel or high power RF EM radiation on the RF channel. A user may interact with the controller 406 via a user interface 452, as discussed above.

The RF channel shown in FIG. 1 comprises an RF frequency source 454 connected to a gate driver 456 that is controlled by the controller 406 via control signal $V_{16}$. The gate driver 456 supplies an operation signal for an RF amplifier 458, which is a half-bridge arrangement. The drain voltage of the half-bridge arrangement is controllable via a variable DC supply 460. An output transformer 462 transfers the generated RF signal on to a line for delivery to the probe 420. A low pass, band pass, band stop or notch filter 464 is connected on that line to protect the RF signal generator from high frequency microwave signals.

A current transformer 466 is connected on the RF channel to measure the current delivered to the tissue load. A potential divider 468 (which may be tapped off the output transformer) is used to measure the voltage. The output signals from the potential divider 468 and current transformer 466 (i.e. voltage outputs indicative of voltage and current) are connected directly to the controller 406 after conditioning by respective buffer amplifiers 470, 472 and voltage clamping Zener diodes 474, 476, 478, 480 (shown as signals B and C in FIG. 1).

To derive phase information, the voltage and current signals (B and C) are also connected to a phase comparator 482 (e.g. an EXOR gate) whose output voltage is integrated by RC circuit 484 to produce a voltage output (shown as A in FIG. 1) that is proportional to the phase difference between the voltage and current waveforms. This voltage output (signal A) is connected directly to the controller 406.

The microwave/measurement channel and RF channel are connected to a signal combiner 114, which conveys both types of signal separately or simultaneously along cable assembly 116 to the probe 420, from which it is delivered (e.g. radiated) into the biological tissue of a patient.

The present invention relates to adaptations or improvements for the microwave channel in the apparatus discussed above.

Figure 2:
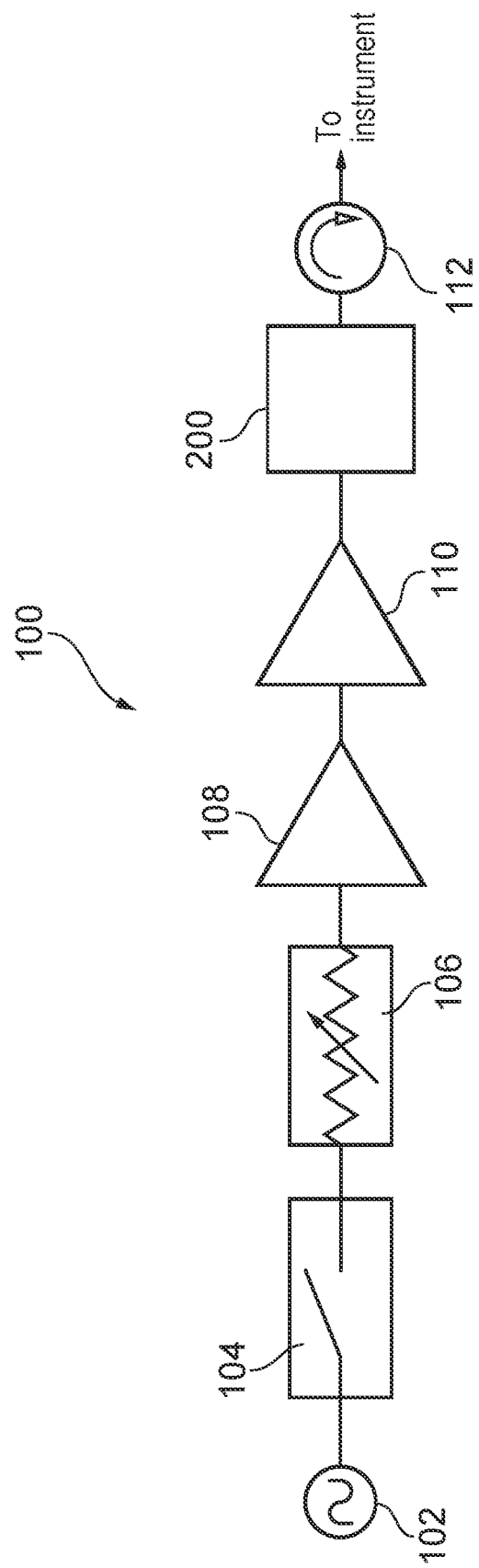
FIG. 2 is a schematic diagram showing an microwave amplifier line up that is an embodiment of the present invention.

FIG. 2 shows a schematic system diagram of a microwave amplifier line up 100 according to an embodiment of the invention. The amplifier line-up 100 may be used as a stand-alone generator, e.g. for circumstances in which only microwave energy is required. Alternatively, the amplifier line-up 100 may be incorporated into a generator of the type discussed above. The amplifier line-up 100 is configured to produce high power pulses of microwave frequency electromagnetic (EM) energy for delivery by an electrosurgical instrument.

The amplifier line-up 100 has a microwave frequency source 102 for generating microwave frequency EM radiation, followed by a signal modulator 104 which may be controlled by an external controller via a source signal (not shown). The modulator 104 modulates the continuous wave output of the microwave source 102 into a series of microwave pulses which are then passed to an attenuator 106. The attenuator 106 may be a variable attenuator which is also controller by a controller via a control signal.

The microwave source 102 may output a signal at a frequency between 5.2 GHz and 5.9 GHz, preferably 5.8 GHz, having a power of 15 dBm or 32 mW, for example. After passing through the modulator 104 and attenuator 106, this microwave signal appears as a train of pulses of a predetermined length, such as 100 μs, with a duty cycle of at least 10%, for example 20% or up to 50%. The attenuator 106 may reduce the power of the microwave pulses to 10 dBm or 10 mW, e.g. based on a feedback loop for controlled power output at the instrument itself. In some embodiments the attenuator 106 may not be present.

The microwave pulses are subject to a number of amplification steps to increase the power to enable effective treatment of biological tissue. A drive amplifier 108 and a power amplifier 110 are used to increase the microwave pulse power to a level which is suitable as an input to an amplifier module 200 (also referred to herein as an amplifier circuit or high power amplifier unit), which is described in more detail below with respect to FIG. 3. In preferred embodiments the input power to the amplifier circuit 200 may be approximately 56.5 dBm or 450 W. Drive amplifier 108 and power amplifier 110 may be chosen so that the output power reaches this level. For example, the drive amplifier 108 may have a gain of approximately 30 dBm and the power amplifier a gain of approximately 16.5 dBm. Alternatively, the power of microwave frequency energy delivered to the amplifier circuit 200 may be lower, such that substantially all of the amplification of the low power microwave signal is a result of the amplifier module 200.

FIG. 2 shows a drive amplifier 108 and a power amplifier 110, but any other combination of components may also be used to increase the power to a level which is suitable as an input to the amplifier circuit 200. For example, in some embodiments the generator 100 may comprise four series connected pre-amplifiers.

After passing through the amplifier module 200, microwave pulses preferably have a power of approximately 63.5 dBm or 2.2 kW. The output of the amplifier circuit 200 is connected to a circulator 112 connected to deliver microwave energy into a coaxial cable (not shown) for sending microwave pulses to the electrosurgical instrument or probe for treatment of tissue. The circulator 112 results in insertion losses of approximately 0.5 dBm such that the power of microwave energy delivered to the instrument is approximately 63 dBm or 2 kW.

Figure 3:
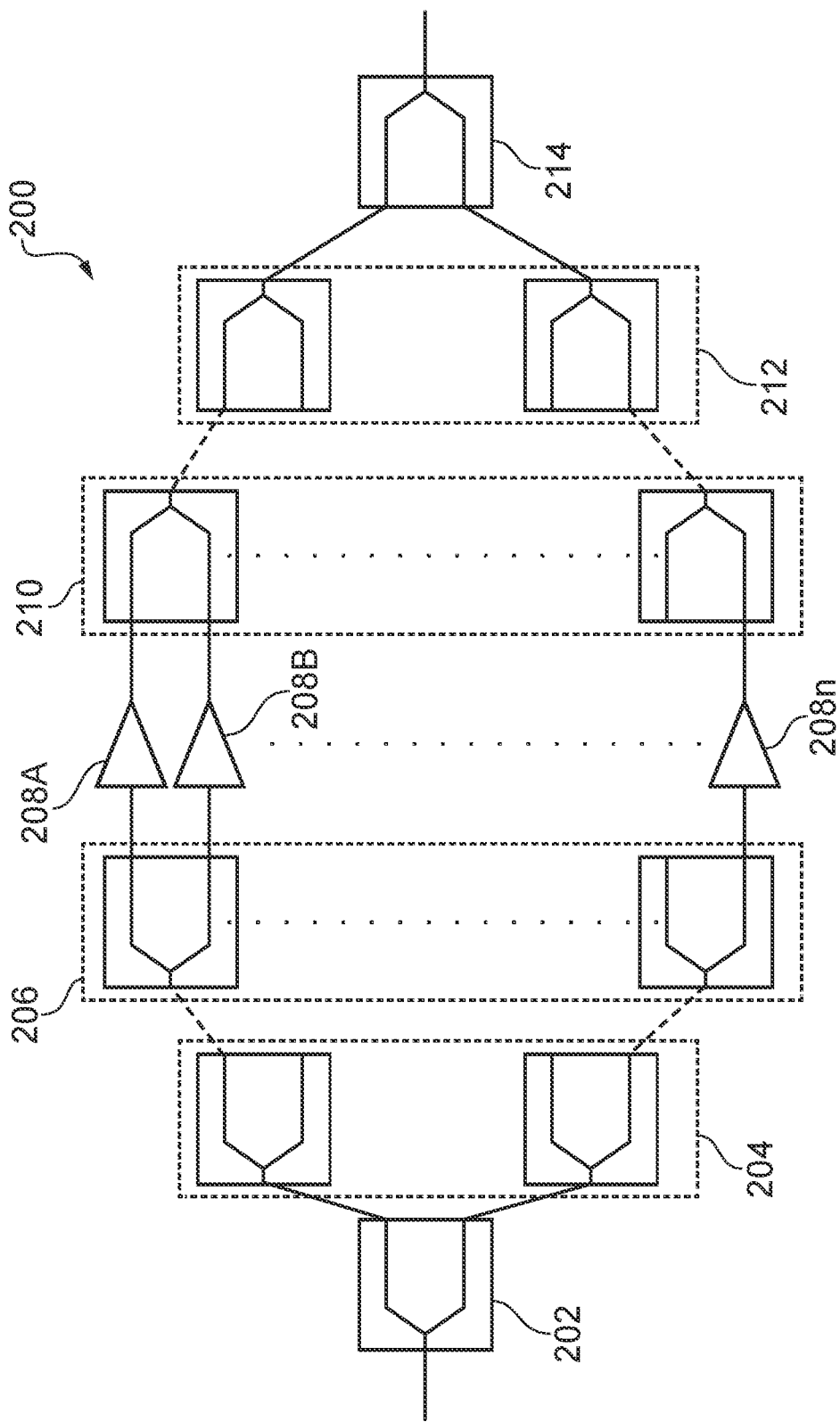
FIG. 3 is a schematic system diagram of an amplifier module that is an embodiment of the present invention.

A schematic diagram of an amplifier module 200 which is suitable for use in generator 100 is shown in FIG. 3. At a general level, the amplifier circuit 200 comprises a series of power dividers 202, 204, 206 which feed microwave energy to a number of amplifiers 208A-208n, the outputs of which are combined to produce a single high power pulsed microwave signal which is provided to an electrosurgical instrument via a coaxial cable.

Microwave pulses from the power amplifier 110 are split into two signals by a first power divider 202. For example, the first power divider 202, and each power divider used in the amplifier circuit 200, may be a Wilkinson power divider which divides an input signal into two equal output signals.

Each output signal from the first power divider 202 is used as an input to a following power divider in a first rank of power dividers 204, which in this embodiment contains two further power dividers. The output signals of each power divider in the first rank 204 may provide an input to each power divider in a further rank of power dividers. The number of power dividers and power divider ranks required is dependent on the number of amplifiers 208A-208n which is chosen. In some embodiments power dividers may split an input signal into more than two outputs, for example at least one of the power dividers may be four-way power divider.

A final rank of power dividers 206 provides input signals for a plurality of amplifiers 208A-208n. For example, in a preferred embodiment there may be eight amplifiers 208A-208n, though the number of amplifiers 208A-208n may be chosen depending on the desired power for an electrosurgical instrument.

Each amplifier 208 may comprise a gallium nitride (GaN) high electron mobility transistor (HEMT), such as a CGHV9350 transistor manufactured by Cree (RTM). At a preferred microwave frequency in the range of 5.2 GHz to 5.9 GHz each amplifier 208 may provide a gain of approximately 10 dBm. However, any suitable amplifier or transistor that provides the requisite gain may be considered.

The output signals of each amplifier 208A-208n are then combined through a series of ranks of power combiners 210, 212, 214. For example, the ranks of power combiners may mirror the power dividers described above. Each power combiner in ranks 210, 212 and 214 may be a Wilkinson power combiner and may preferably be a two-way power combiner, though four-way power combiners may also be used. By combining the output signals of each amplifier 208A-208n, a series of high power microwave pulses are produced by the amplifier circuit 200. These high power pulses are fed to an electrosurgical instrument or probe, for example via a coaxial cable, for treatment of biological tissue.

A particularly preferred embodiment of an amplifier module 200 will now be described with reference to FIG. 3, assuming an input microwave power of 56.5 dBm or 450 W. A preferred embodiment of the invention comprises eight amplifiers 208A-208n, each having a gain of approximately 10 dBm. Each power divider described herein splits an input signal into two output signals each having a power which is 3 dBm lower than that of the input signal, and is assumed to result in additional insertion losses of approximately 0.5 dBm.

The first power divider 202 takes the input microwave signal having a power of 56.5 dBm and splits the signal between two branches, each having a microwave power of 53 dBm. A first rank of power dividers 204 contains two power dividers, such that the output of the first rank of power dividers 204 is four signals each having a microwave energy of 49.5 dBm. The final rank 206 contains four power dividers, the output of which is eight signals each having a microwave energy of 46 dBm. Each of these eight signals is provided as the input to a respective amplifier 208A-208n, which amplifies the received microwave signal to a power of 56 dBm, or approximately 400 W. The total power output of the eight amplifiers 208A-208n is therefore approximately 3.2 kW.

The output signals of the eight amplifiers 208A-208n are then combined through a series of power combiners. Each power combiner described herein combines two input signals into one output signal having a power which is 3 dBm higher than that of the input signal, before insertion losses of approximately 0.5 dBm.

The outputs of the eight amplifier 208A-208n are sent to a first rank of power combiners 210, which contains four power combiners. The output of the first rank 210 is four signals each having a microwave energy of 58.5 dBm. These four signals are provided as inputs to a second rank of power combiners 212, containing two power combiners, resulting in two signals having microwave energy of 61 dBm. A final power combiner 214 gives a single output of the amplifier circuit 200, having a microwave power of approximately 63.5 dBm or 2.2 kW.

By providing a cascade of amplifiers whose gain outweighs the splitter losses as outlined above, a microwave signal in the form of a train of high power, short duration pulses of microwave EM energy can be obtained.

By providing an amplifier module 200 in an electrosurgical apparatus in this way, electrosurgical treatment may be performed in substantially less time than with known generators. For example, approximately 2 kJ of energy needs to be delivered to biological tissue for effective ablation treatment. For pulsed microwave frequency energy operating at a power of 2 kW, if each pulse of energy has a duration of 100 μs and the apparatus operates with a 50% duty cycle, biological tissue can be ablated in approximately 2 seconds. If the duty cycle is reduced to 20%, ablation takes approximately 5 seconds; and with a 10% duty cycle ablation may take approximately 10 seconds.

In general, reducing treatment time can minimize unwanted heating effects caused by energy losses, e.g. along the length of a cable carrying the microwave signal to the treatment site. By delivery the requisite energy in short pulse, the present invention may further reduce the heating of the coaxial cable because the thermal response of the cable cannot react to the magnitude of the power within the time frame of the pulse duration. Consequently, for a given amount of energy conveyed by the cable, there may be less heat lost if that energy is transmitted as a series of short high power pulses than if it is transmitted as a lower power continuous waveform.

As a result of the energy delivery technique present herein, smaller diameter coaxial cables can be used to delivery a given energy payload, thereby allowing insertion into smaller diameter body cavities for electrosurgery.

The pulsed nature of the signal may also assist in avoiding problems with perfusion and other natural mechanisms which arise as a patient's body response to heating caused by ablation or other treatment.

The invention claimed is:

1. An electrosurgical generator comprises an amplifier line-up that comprises:
    a microwave signal generator for generating microwave electromagnetic (EM) radiation;
    a modulator arranged to pulse the microwave EM radiation; and
    an amplifier module connected to the modulator and arranged to increase the power of the pulses of the microwave EM radiation received therefrom, the amplifier module comprising an array of amplifiers connected in parallel, wherein output signals from the array of amplifiers are combined to produce an output microwave signal; and
    a feed structure for conveying the output microwave signal to a probe,
    wherein the modulator is configured to cause the output microwave signal to comprise a series of microwave pulses having a duty cycle equal to or less than 20%, wherein each microwave pulse has a duration equal to or less than 0.1 s, and
    wherein the amplifier module comprises:
    a power divider unit arranged to receive the pulses of the microwave EM radiation from the modulator and split them into input signals for the array of amplifiers, wherein the power divider unit comprises a plurality of cascaded power dividers arranged in two or more ranks; and
    a power combiner unit arranged to combine the output signals from the array of amplifiers,
    wherein the power combiner unit comprises a plurality of cascaded power combiners arranged in two or more ranks which mirror the two or more ranks of the plurality of cascaded power dividers.

2. The electrosurgical generator of claim 1 comprises a drive amplifier connected between the modulator and the amplifier module.

3. The electrosurgical generator of claim 1, wherein the series of microwave pulses each has a power equal to or greater than 400 W.

4. The electrosurgical generator of claim 1, wherein the series of microwave pulses each has a power equal to or greater than 2 kW.

5. The electrosurgical generator of claim 1, wherein each microwave pulse has a duration equal to or less than 1 ms.

6. The electrosurgical generator of claim 1, wherein the array of amplifiers comprises eight amplifiers.

7. The electrosurgical generator of claim 1, wherein each amplifier in the array of amplifiers comprises high electron mobility transistors.

8. The electrosurgical generator of claim 7, wherein the transistors are gallium nitride transistors.

9. The electrosurgical generator of claim 1, wherein each amplifier in the array of amplifiers has a gain equal to or greater than 10 dBm.

10. The electrosurgical generator of claim 1, wherein the output signal from each amplifier has power of 400 W.

11. The electrosurgical generator of claim 1, wherein the feed structure comprises a coaxial cable having a diameter equal to or less than 3 mm.

* * * * *